(12) United States Patent  
Kristensen et al.

(10) Patent No.: US 8,221,359 B2  
(45) Date of Patent: Jul. 17, 2012

(54) INJECTION DEVICE WITH CAP

(75) Inventors: Johnny Kristensen, Roskilde (DK); Jim Radmer, Fredensborg (DK); Peter Christian Klitgaard, Smørum (DK)

(73) Assignee: Novo Nordisk A/S, Bagsvaerd (DK)

( * ) Notice: Subject to any disclaimer, the term of this patent is extended or adjusted under 35 U.S.C. 154(b) by 251 days.

(21) Appl. No.: 11/663,185

(22) PCT Filed: Sep. 8, 2005

(86) PCT No.: PCT/EP2005/054437  
§ 371 (c)(1),  
(2), (4) Date: Jun. 17, 2008

(87) PCT Pub. No.: WO2006/032614  
PCT Pub. Date: Mar. 30, 2006

(65) Prior Publication Data  
US 2008/0306449 A1    Dec. 11, 2008

Related U.S. Application Data

(60) Provisional application No. 60/617,342, filed on Oct. 7, 2004.

(30) Foreign Application Priority Data

Sep. 24, 2004    (EP) .................................... 04022740

(51) Int. Cl.  
*A61M 5/32* (2006.01)

(52) U.S. Cl. ........ 604/192; 604/110; 604/155; 604/207; 604/198

(58) Field of Classification Search ................. 604/192, 604/198, 110, 506, 155, 207–211  
See application file for complete search history.

(56) References Cited

U.S. PATENT DOCUMENTS

| | | | |
|---|---|---|---|
| 5,041,086 A * | 8/1991 | Koenig et al. ................... 604/65 |
| 5,348,539 A | 9/1994 | Herskowitz | |
| 5,728,074 A * | 3/1998 | Castellano et al. ........... 604/207 |
| 5,928,197 A * | 7/1999 | Niehoff ........................ 604/155 |
| 5,993,423 A * | 11/1999 | Choi ............................. 604/155 |
| 6,042,565 A * | 3/2000 | Hirschman et al. ........... 604/155 |
| 6,277,098 B1 | 8/2001 | Klitmose et al. | |

(Continued)

FOREIGN PATENT DOCUMENTS

| | | | |
|---|---|---|---|
| JP | 2004516111 | | 6/2004 |
| WO | 02/051477 | | 7/2002 |
| WO | WO-02/051477 | * | 7/2002 |
| WO | WO02051477 | * | 7/2002 |
| WO | WO 02051480 | | 7/2002 |
| WO | 03/057286 | | 7/2003 |

*Primary Examiner* — Bhisma Mehta  
*Assistant Examiner* — Edelmira Bosques  
(74) *Attorney, Agent, or Firm* — Wesley A. Nicolas; Marc A. Began; Reza Green

(57) ABSTRACT

A drug delivery device capable of working in at least two different modes which includes a dose injection mode and a set-up mode. The drug delivery device automatically changes from the dose injection mode to the set-up mode and vice versa in accordance with the detection of the cover by a cover detection switch. In the dose injection mode doses can be set and injected; in the set-up mode various parameters assisting the use of the drug delivery device can be set. This setting is preferably done by selecting the parameters from a menu, also in this mode historical data stored in the device can be viewed.

5 Claims, 4 Drawing Sheets

U.S. PATENT DOCUMENTS

| | | | |
|---|---|---|---|
| 6,485,465 B2 * | 11/2002 | Moberg et al. | 604/154 |
| D476,734 S * | 7/2003 | Pavlu et al. | D24/114 |
| 6,726,661 B2 * | 4/2004 | Munk et al. | 604/207 |
| 7,377,907 B2 * | 5/2008 | Shekalim | 604/134 |
| 2003/0083626 A1 | 5/2003 | Munk et al. | |
| 2004/0024364 A1 | 2/2004 | Langley et al. | |
| 2004/0030298 A1 * | 2/2004 | Veasey et al. | 604/208 |
| 2005/0090781 A1 * | 4/2005 | Baba et al. | 604/209 |

* cited by examiner

INJECTION DEVICE WITH CAP

CROSS-REFERENCE TO RELATED APPLICATIONS

This application is a 35 U.S.C. §371 national stage application of International Patent Application PCT/EP2005/054437 (published as WO 2006/032614), filed Sep. 8, 2005, which claimed priority of European Patent Application 04022740.7, filed Sep. 24, 2004; this application further claims priority under 35 U.S.C. §119 of U.S. Provisional Application 60/617,342, filed Oct. 7, 2004.

THE TECHNICAL FIELD OF THE INVENTION

The present invention generally relates to an apparatus for delivering liquid medicine to the human body preferably in a subcutaneous way and more specifically to an electronically controlled apparatus.

DESCRIPTION OF RELATED ART

In the disclosure of the present invention reference is mainly made to the treatment of diabetes by injection or infusion of insulin; however this is only an exemplary use of the present invention.

Portable drug delivery apparatuses for delivering a drug to a patient are well known and generally comprise a reservoir adapted to contain a liquid drug and having an outlet in fluid communication with a hollow needle, as well as expelling means for expelling the drug out of the reservoir and through the skin of the patient via the hollow needle. The delivery apparatus may be adapted for discrete use, i.e. injection of an amount of a drug a given number of times during the day through a needle temporarily inserted into the patient, or they may be adapted for continuous delivery of the drug through a permanent fluid connection between the delivery apparatus and the patient. The former type of device is often referred to as an injection device and the latter type is often termed an infusion pump.

A prior art injection device is disclosed in WO 02/051477. This injection device is provided with an electric motor which is used to press out a dose of medicine to be injected. The size of the dose to be pressed out is set by operating two dose setting buttons, one for dialling up the dose and one for dialling down the dose. The set dose is shown in a display panel. In order to inject the set dose the user operates an injection button after first having pressed down a confirmation button to confirm the size of the dose. Further the disclosed injection device comprises a cover and a cover detection switch able to detect the presence of a cap or cover.

An infusion pump for continuously delivering insulin to a human body is disclosed in EP 980.688. This infusion pump further has the ability to inject a bolus dose of insulin. The control circuit controlling the pump is able to work in a plurality of different modes. One of the modes is a doctor mode which allows a doctor or physician access to set a number of parameters. In order to switch to the doctor mode, a separate button or a combination of buttons must be pressed and the return to the general mode requires the user to select the required mode from a menu.

U.S. Pat. No. 6,277,098 discloses an injection device with a housing, operating means, a cap, switches and an electronic circuit adapted to monitor the functionality of the device. A series of possible combinations of signals from the switches are put in the memory of the electronic circuit. Should a switch signal combination which is not in the memory occur, the electronic circuit will switch off the presentation of the operational condition of the device, thereby securing that the user does not inject a wrong dose of medicine, caused by a malfunction of the switches. Accordingly the injection device disclosed in U.S. Pat. No. 6,277,098 can switch between an operational condition and an error condition, depending on whether a whole pattern of signals received by the electronic circuit are allowed or not.

The injection device disclosed in US 2003083626 also has a housing, an electronic circuit, operating means, a cap and cover detection means. The injection device according to US 2003083626 can shift between a dose injection mode and an air shot mode. The air shot mode includes the function: air shot, immediate prior to an injection. To switch to injection mode the dose setting button has to be operated.

WO 03057286 describes a delivery device comprising a housing, an electronic circuit, operating means, a cap and cover detection means. Together with other signals, the cap switch signal is used to generate a reminder to the user to perform an air shot prior to an injection.

Electronic delivery devices of today are very similar to cellular telephones in that respect that a number of parameters must be set up. Usually such parameters are set prior to the first use, however they are frequently changed and must be accessible at any time. Further it is usually possible to view various historical data stored. The parameters to be set in an electronic delivery device could e.g. be very general parameters such as languages of use and date and time or it could be more specific parameters such as type of medicine and maximum dose to be injected. Further different alarms alerting the user could be set.

Some drugs, such as insulin are self-administered, and the typical diabetes person will require subcutaneous injections of insulin several times during the course of the day. Since most injections of these drugs are performed in private surroundings by the user himself there is a great desire for very simple injection devices. At the same time there is also a great desire for delivery devices having an advanced functionality.

DESCRIPTION OF THE INVENTION

Having regard to the above-identified prior art devices, it is an object of the present invention to provide a drug delivery device in which the user can inject a liquid drug in a simple and straight forward manner and at the same time gain access to a variety of advanced functions without interfering with the simplicity of the injection device.

It is further an object of the present invention to provide a drug delivery device which solves the problem arising in the prior art devices where the provided advanced functions added to the function of delivering a drug complicates the simple, user-friendly manner of delivering a drug and therefore lowers the safety of the delivery process. The present invention solves this problem by always switching the device to a simple and safe injection mode when the cap is taken off the device. This means automatically switching to a simple and safe injection mode without the necessity of operating any operating means which has to remembered or read, but simply switching when the cap is taken off, a logical and self-evident move made by the user when wanting to inject a drug.

Claim 1

Correspondingly, a drug delivery device is provided, comprising an electronic circuit for controlling the operation of the device. Such electronic circuit would usually be an ASIC including a programmable micro processor having both memory functionality and input/output function. Further the drug delivery device comprises operating means for setting the size of a dose to be injected and for executing the injection. The electronic circuit is designed to work in a number of different modes including an injection mode and a set-up mode. In the injection mode the drug delivery device functions as a traditional injection device where a dose to be injected can be selected and injected using the operating means. In the set-up mode, the user can gain access to a plurality of more advanced functions which are preferably selected from a menu displayed in a display panel using the operating means.

The operating means for operating the drug delivery device in the dose injection mode can be located at one position and the operating means for operating the drug delivery device in the set-up mode can be located in a different position, or the operating means can be shared as explained later.

The drug delivery device is provided with a cover fully or partly covering the drug delivery device. Cover detection means are also provided which are able to detect the presence of the cover and to inform the electronic circuit whether the cover is mounted on the drug delivery device or not. Such cover detection means can either be a mechanical on/off switch or it can be a detector such as a photo electric sensor, an inductive sensor or a hall element.

This information is used by the electronic circuit to switch between the modes such that the drug delivery device is in the injection mode when the cap switch is off with no cover present and in the set-up mode when the cover switch is on with the cover present.

When a user wants to set-up the advanced functions of the drug delivery device the user simply has to leave the cover mounted on the device and use the operating means to set-up the various functions. If the user for some reason wants to abort the set-up mode and perform an injection all that is required is to remove the cover and the device will switch to injection mode and a different or the same set of operating means will be available for dialling up a dose.

This is very beneficial since the user will not be prevented from taking his injection while being involved in an advanced set-up. When it is time to perform an injection simply removing the cover returns the drug delivery device to a well known condition ready for injection. Further should an incident occur which requires a non-instructed third party that are not familiar with all the features of the device to perform an injection, removal of the cover will bring the device into the very simple and straight forward injection mode. Finally using the cover switch to also switch between the modes secures that all non insulin handling will be done with the cover mounted and the needle covered. This prevents a user from accidentally executing a non-controlled injection with the device in the set-up mode.

Claim 2-4

In order to minimize the number of buttons on the drug delivery device, the same buttons can be dedicated to different use in the different modes.

The dose setting button used for setting the size of the dose to be injected in the dose injection mode can be used to scroll through a menu of set-up parameters in the set-up mode. The accept button used to accept the set dose in the dose injection mode can be used to select from the menu in the set-up mode. The escape button is preferably used for escaping backwards in the menu in the set-up mode and the injection button is preferably used for injecting the set and accepted dose.

The button for dialling the size of the dose can either comprise two separate buttons as disclosed in WO 02/051477 or one multifunctional button. When the size of the dose desired has been the set, the user must activate an accept button in order to accept the set dose. Only when the set dose has been approved will the electronic circuit be permitted to expel the set dose. Such accept button is more detailed disclosed in FIG. 8 in U.S. Pat. No. 4,006,736, which is hereby incorporated by reference. When the dose has been set and confirmed it is injected by activating the injection button.

Alternatively to fully or partly using the same buttons in the different modes, a number of separate buttons for use in the injection mode could be located in a position covered by the cap when mounted.

Claim 5

In the set-up dose a great number of different parameters can be set. These parameters could e.g. include:
Languages of use
Date and time
Insulin type
Maximum dose size
Maximum daily quantity
Alarm functions Claim 6

Data relating to the size of doses injected paired with the time of the injections is preferably stored in the drug delivery device and can be recalled and viewed when the drug delivery device is in the set-up mode.

Further, the device can be provided with means for receiving various data from a remote device e.g. a second drug delivery device loaded with a different type of insulin. With these data available in the drug delivery device the user can when in the set-up mode view different logs of data.

DEFINITIONS

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

All headings and sub-headings are used herein for convenience only and should mot be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 2 Shows a drug delivery device with the cover mounted on.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
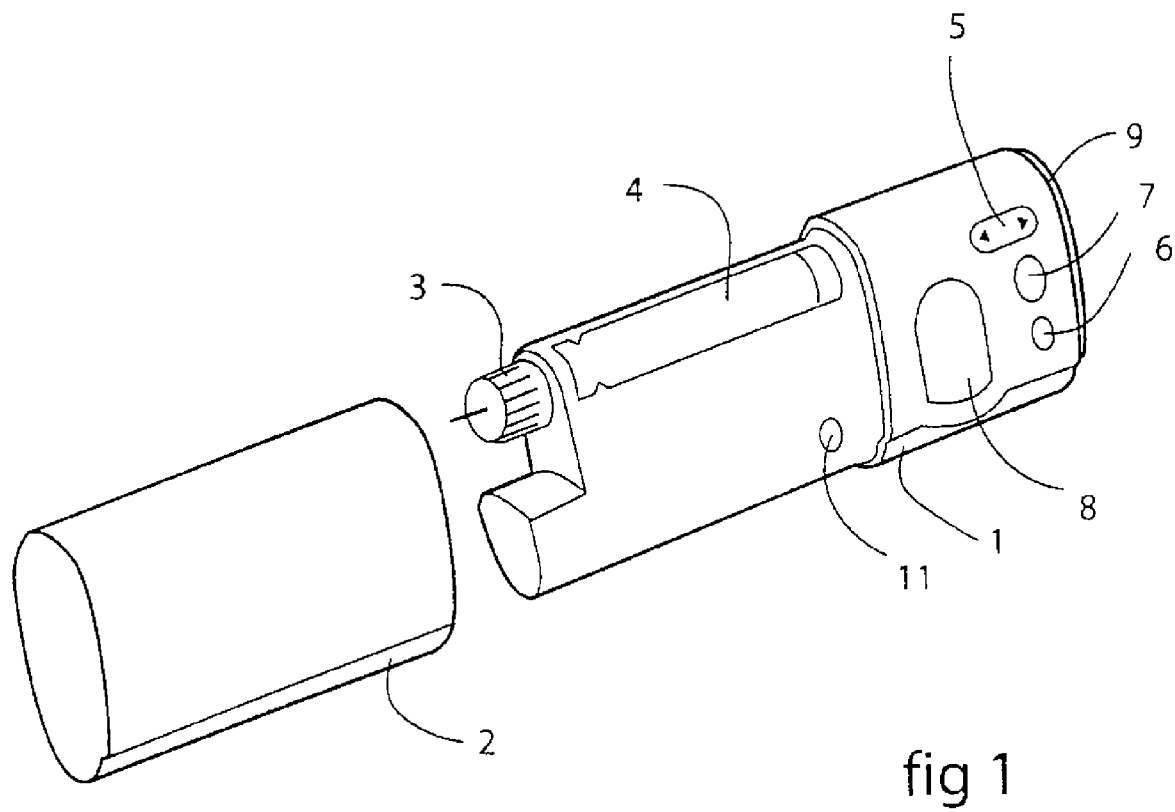
FIG. 1 Shows a drug delivery device with the cover dismounted.
Figure 2:
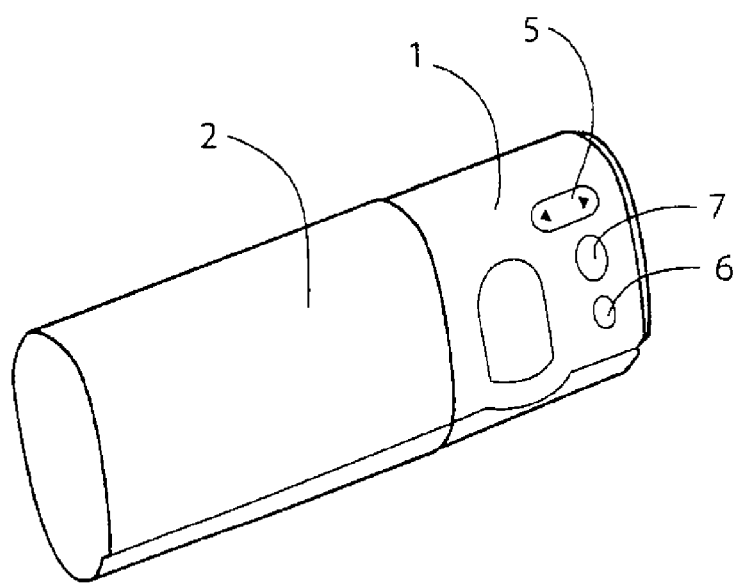

FIG. 1 discloses an electronic injection device comprising a housing 1 and a cover or cap 2 which is adapted to cover the distal part of the housing 1. An injection needle 3 is connected to the distal end of the housing 1 and communicates with a reservoir 4 containing the drug to be injected. When the cap 2 is mounted as disclosed in FIG. 2 the injection needle 3 is also covered by the cap 2.

Left uncovered by the cap 2 is a plurality of operating buttons 5, 6, 7, 9 comprising a dose setting button 5 for setting a dose to be injected, an accept button 6 for accepting the dialled dose, an escape button 7 and an injection button 9.

Figure 3:
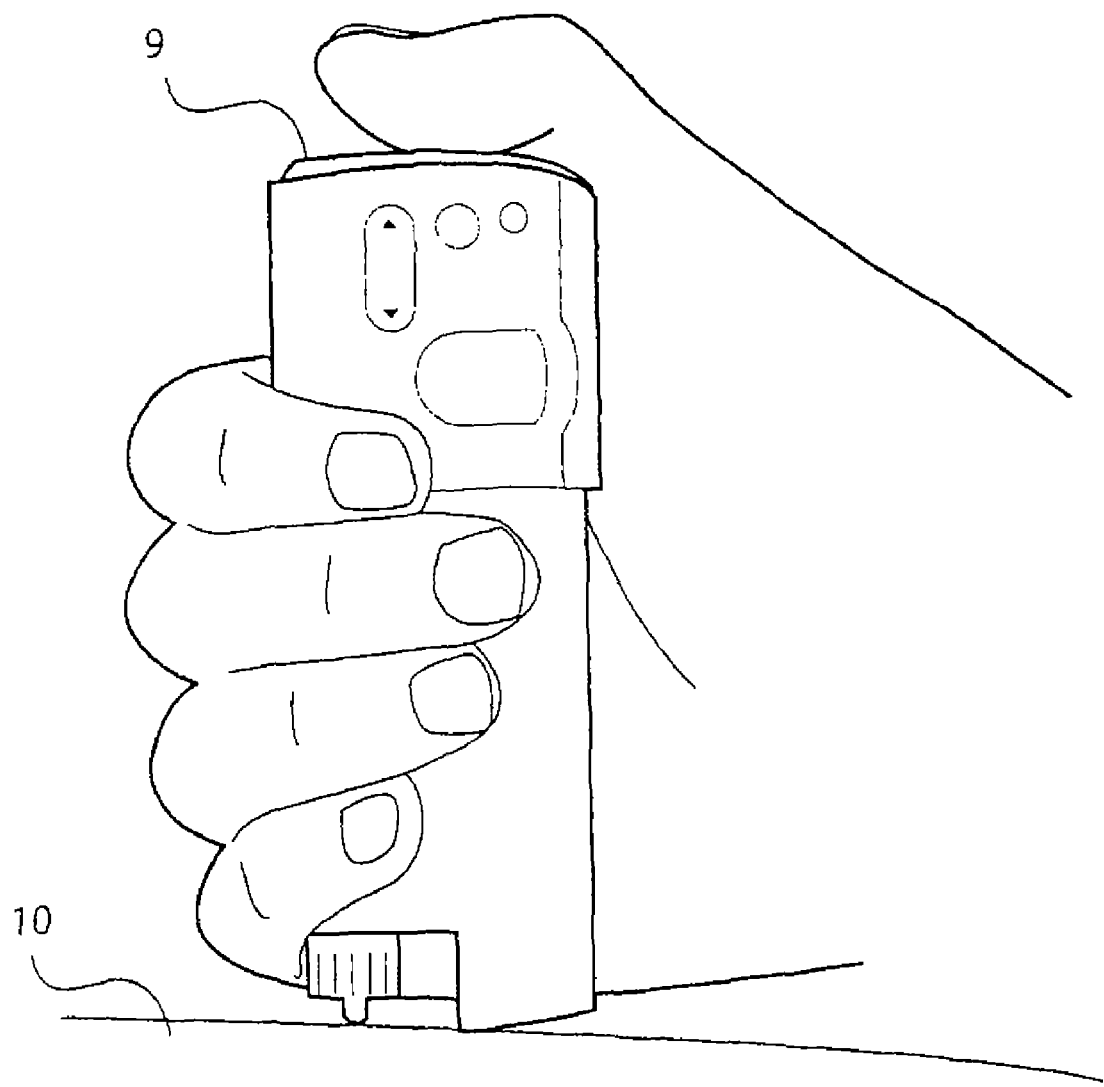
FIG. 3 Shows a drug delivery device during injection.

In order to perform an injection the user removes the cap 2 and dials the size of the dose to be injected using the dial up/dial down button 5. As the dose is dialled, the size of the dose is displayed in the display panel 8. When the set dose is dialled to an adequate size, the user operates the accept button 7 thereby confirming the set dose. After having inserted the injection needle 3 into the tissue 10 as disclosed in FIG. 3, the user operates the injection button 9 to release the set dose.

The area of the drug delivery device covered by the cap 2 when mounted is provided with a cover detection switch 11 which is able to detect the presence of the cap 2.

Figure 4:
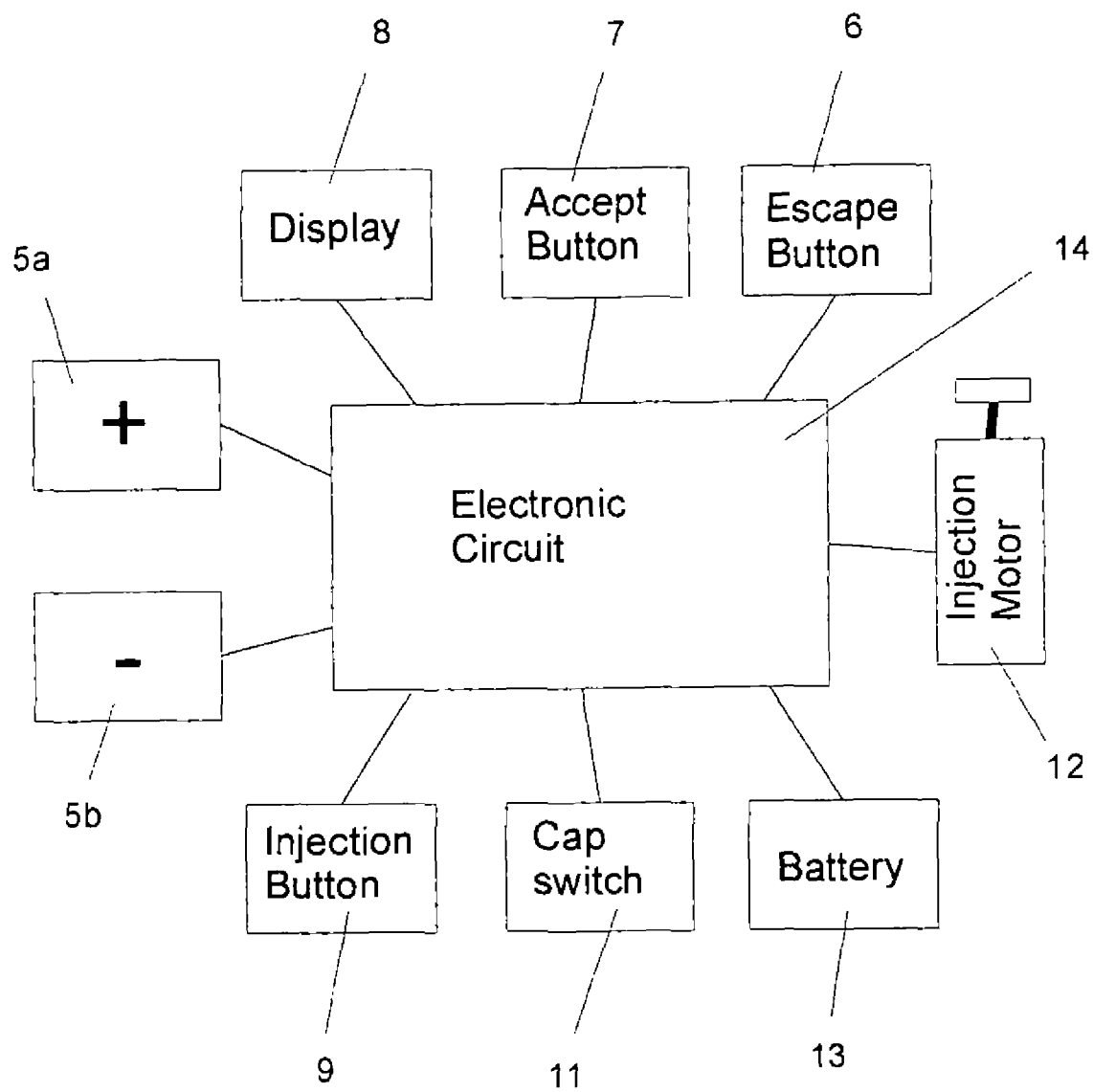
FIG. 4 Shows a block diagram of the electronic components.

The electronic circuit 14 which is schematic illustrated in FIG. 4 is connected to a battery 13 which drives an injection motor 12 to inject the predetermined dose. The predetermined dose is set by operating the dose setting button 5, which in FIG. 4 is depictured as a first button 5a for dialling up the dose and a second button 5b for dialling down the dose. The dose setting button 5 could however be formed as one multifunctional button as disclosed in FIG. 1-3 or alternatively as a rotational button, a soft-key, a joystick or a wheel.

As the dose is set the numerical value is displayed in the display panel 8. When the correct dose has been dialled, the user activates the accept button 7 which allows current to flow from the battery 13 to the injection motor 12 once the injection button 9 is operated.

Figure 5:
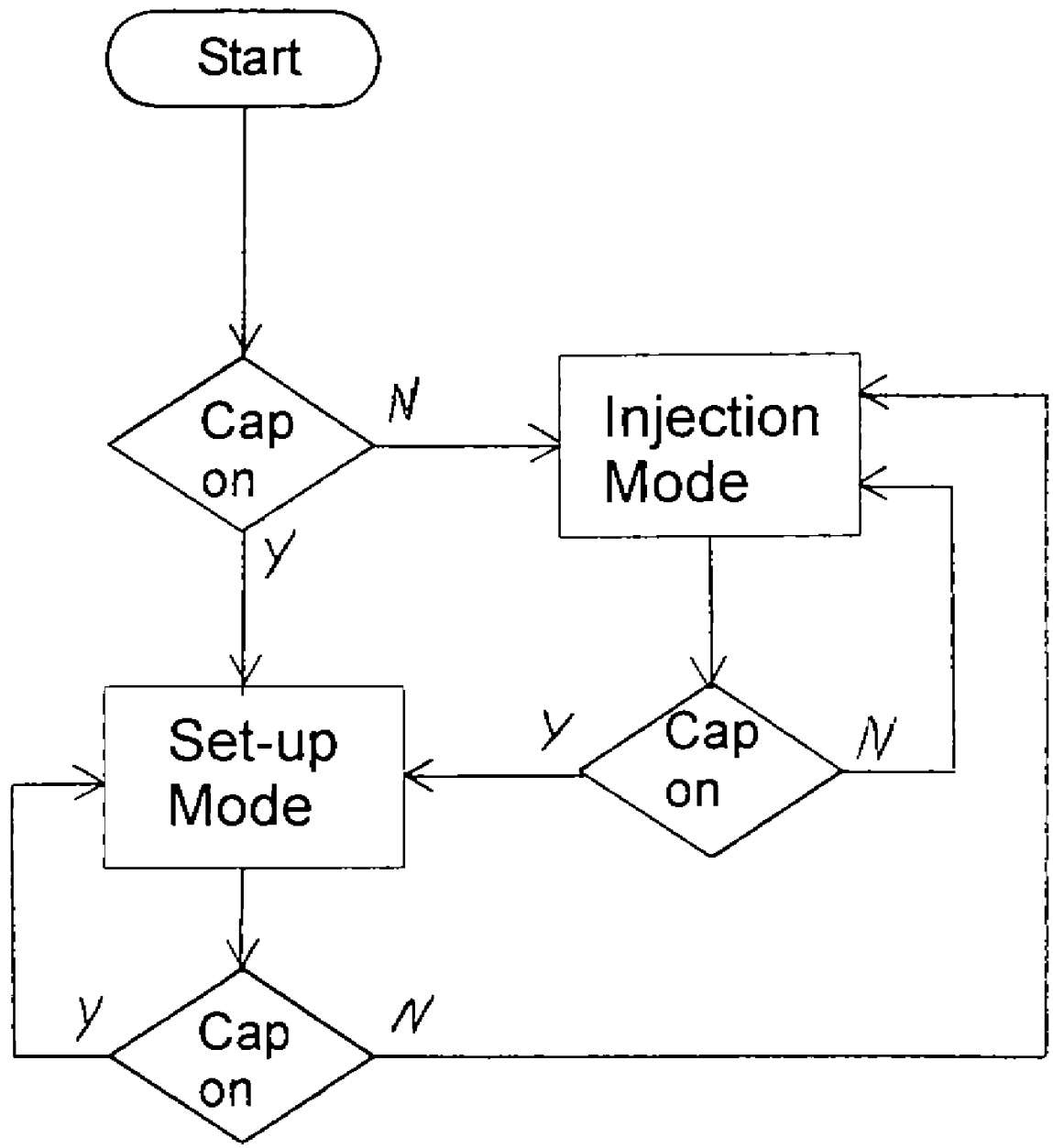
FIG. 5 shows a flowchart of switching between modes.

The cap switch 11 detects if a cap 2 is present as an on or off signal. As illustrated in FIG. 5, the electronic circuit 14 works in the injection mode if the cap 2 is not present and in the set-up mode if the cap 2 is present. The presence of the cap 2 is enquired by the electronic circuit 14 both when the drug delivery device is switched on and continuously during operation as illustrated in FIG. 5.

In the disclosed configuration, the dose setting button 5 is used to set the size of the dose to be injected and the accept button 7 is used to confirm the set size when the drug delivery device is in the injection mode.

In the set-up mode the user can use the dose setting button 5 to scroll through a menu containing the different parameters, the accept button 7 to select from the menu, and the escape button 6 to move backwards in the menu.

Further historical data e.g. relating to past injections is automatically stored a memory in the drug delivery device in a well known manner. These stored data can be viewed when the drug delivery device is in the set-up mode by selecting them from the menu and scrolling through the historical data using the dose setting button 5.

Some preferred embodiments have been shown in the foregoing, but it should be stressed that the invention is not limited to these, but may be embodied in other ways within the subject matter defined in the following claims. The number of modes available could e.g. be higher than two. A special mode only accessible by a registered doctor could be added without changing the scope of the annexed claims.

The invention claimed is:

1. A drug delivery device, comprising:
a housing having a battery compartment and proximal and distal ends;
  the proximal end includes:
    an operator selection panel,
    a display panel that displays the operator selections, and
    an electronic circuit, powered by the battery, which receives the operator selections as displayed on the display panel and outputs a control signal to a driver motor;
  the distal end includes:
    a drug reservoir, and
    a removable injection needle that are operatively connected to the drive motor and a cover detector;
a removable cover that encloses the distal end and overlies the cover detector when assembled on the housing,
wherein the electronic circuit further comprises:
  a set-up mode when the cover is overlying the cover detector, and
  a dose injection mode when the cover detector is uncovered and an injection option is operated,
wherein the operator selection panel used to set the size of a dose to be injected when in the dose injection mode, and the operator selection panel used to set a number of parameters on the display panel when in the set-up mode are at least partly the same, and
wherein when the electronic circuit is in set-up mode it allows the display panel to indicate different operator selections, which operator selections are not available on the display panel in dose injection mode.

2. A drug delivery device as in claim 1, wherein a number of parameters can be set in the set-up mode, the parameters including one or more of the following parameters:
languages of use
date and time
insulin type
maximum dose size
maximum daily quantity
alarm functions.

3. A drug delivery device as in claim 1, wherein historical data stored can be viewed in the set-up mode.

4. A drug delivery device as in claim 1, wherein the operator selection panel includes a dose setting option, an escape option, an accept option, and the injection option.

5. A drug delivery device as in claim 1, wherein the operator selection panel includes multiple separate dedicated buttons.

* * * * *